US005263477A

United States Patent [19]

Crome

[11] Patent Number: 5,263,477

[45] Date of Patent: Nov. 23, 1993

[54] CHEMICAL AND BIOLOGICAL WARFARE FILTER INJECTOR MECHANISM

[75] Inventor: Victor P. Crome, Davenport, Iowa

[73] Assignee: Litton Systems, Inc., Davenport, Iowa

[21] Appl. No.: 874,157

[22] Filed: Apr. 27, 1992

[51] Int. Cl.[5] .......................... A62B 9/02; A62B 7/04; A61M 16/00; F16K 31/26

[52] U.S. Cl. .......................... 128/205.24; 128/205.11; 128/204.25; 128/204.29; 137/494

[58] Field of Search ...................... 128/201.24, 201.25, 128/201.28, 204.26, 204.29, 205.12, 205.24, 205.25, 206.12, 207.12, 205.11, 204.25; 137/494

[56] References Cited

U.S. PATENT DOCUMENTS

| | | | |
|---|---|---|---|
| 2,824,557 | 2/1958 | Mejean et al. | 128/201.28 |
| 3,474,812 | 10/1969 | Robertson | 128/204.29 |
| 4,404,969 | 9/1983 | Cresswell et al. | 128/201.28 |
| 4,651,728 | 3/1987 | Gupta et al. | 128/201.28 |
| 4,676,236 | 6/1987 | Piorkowski et al. | 128/201.25 |
| 4,741,332 | 5/1988 | Beaussant | 128/201.23 |
| 4,856,507 | 8/1989 | Ouillon et al. | 128/204.29 |

FOREIGN PATENT DOCUMENTS 0050052 4/1982 European Pat. Off. .

*Primary Examiner*—Edgar S. Burr
*Assistant Examiner*—Kimberly L. Asher
*Attorney, Agent, or Firm*—Brian L. Ribando

[57] ABSTRACT

An injector mechanism uses breathing system gas to entrain cabin air to demist and defog the hood and visor of an aircrew chemical and biological warfare ("CBW") suit. The injector includes a needle valve for flow rate adjustment and an aneroid for altitude compensation. The CBW filter is downstream of the negative pressure produced by the injector to purify any ambient air drawn into the system at the negative pressure region. Positive pressure in the system downstream of the CBW filter prevents inward leakage and contamination of the demist and defog gas stream.

2 Claims, 1 Drawing Sheet

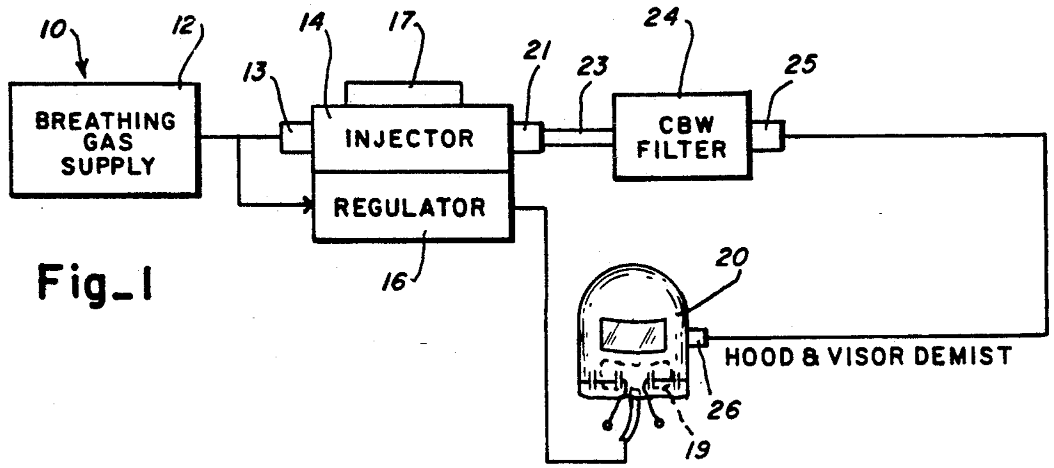
Fig_1
Fig_2
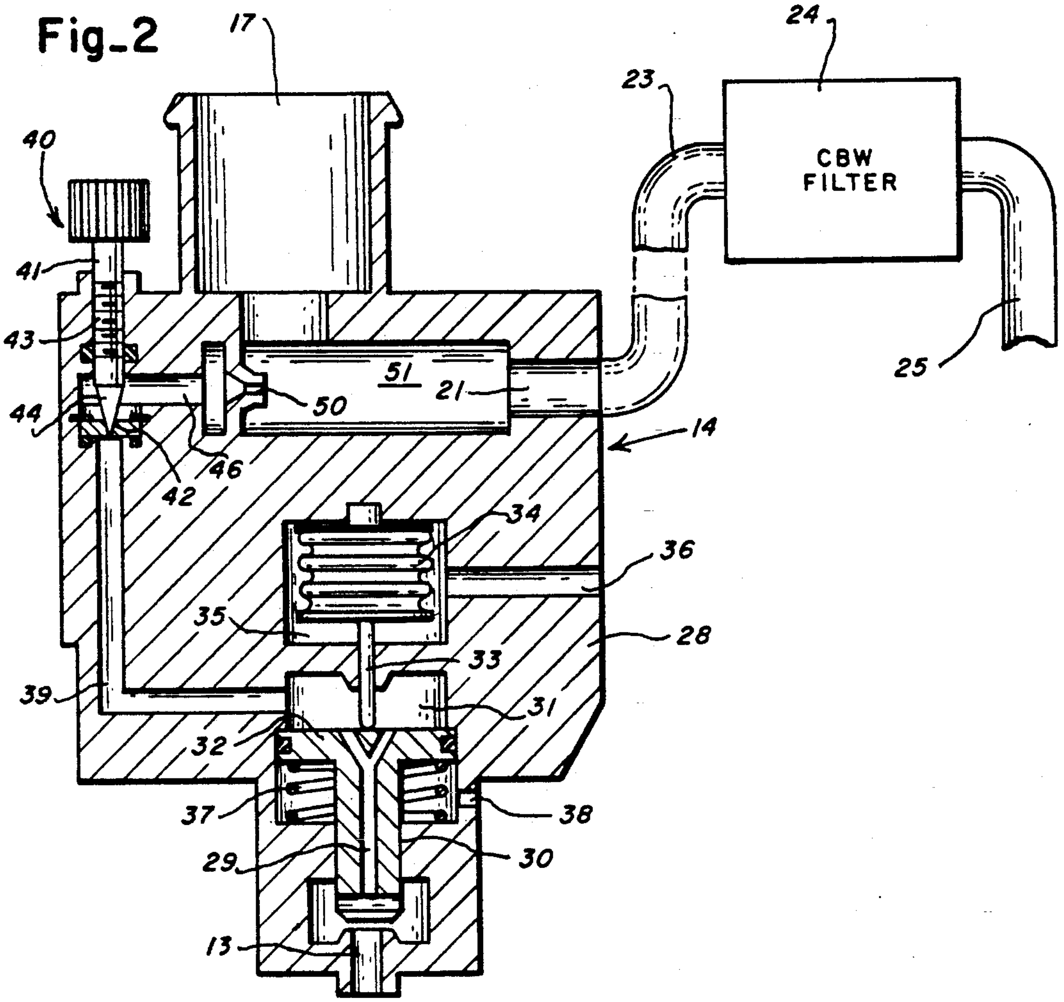

CHEMICAL AND BIOLOGICAL WARFARE FILTER INJECTOR MECHANISM

BACKGROUND OF THE INVENTION

The present invention relates to an injector mechanism used to demist and defog the hood and visor of an aircrew chemical and biological warfare ("CBW") respirator system.

Currently, most aircrew CBW respirator systems utilize either a motor driven filter-blower, or 100 percent breathing gas to supply the gas flow to demist and defog the aircrew respirator hood and visor assembly. Each of these methods has certain drawbacks.

The use of a motor driven filter-blower unit is useful in providing a safe source of breathing and demist gas while the aircrew is entering and exiting the aircraft. However, once the aircrew is in the aircraft, a filter-blower is cumbersome to stow in the cockpit during flight and has a limited battery life. Also, a filter-blower can only be used to supply breathing gas if the aircraft is scheduled for a mission below an altitude of about 10,000 feet since filtered cabin air does not contain a sufficient oxygen concentration for prolonged aircrew breathing at the higher altitudes.

A second method uses 100 percent breathing gas (oxygen) for demist and defog purposes. This consumes the liquid oxygen ("LOX") or high pressure gaseous oxygen ("GOX") breathing gas supply and can result in a restricted flight duration capability for the aircraft. Using 100 percent breathing gas for demist and defog from an on board oxygen generating system ("OBOGS") equipped aircraft does not limit the flight duration because of the unlimited supply available. However, it requires the OBOGS to be considerably larger in order to accommodate the demist flow requirements while maintaining the required breathing gas at minimum oxygen concentration levels.

One prior art system shown in U.S. Pat. No. 4,741,332 uses an injector to entrain cabin air which is drawn through a CBW filter and used for demist and defog purposes The injector is downstream of the CBW filter; however, and the negative pressure (suction) which is created by the injector allows the possibility of inward chemical agent leakage at the junctions of system components with resulting contamination of the demist and defog gas stream.

It would, accordingly, be desirable to provide a demist system to provide physiologically safe oxygen demist and breathing gas while minimizing the demand on the oxygen supply source so as to not reduce the flight capability of the aircraft or require an oxygen supply system having substantially greater capacity. It would be further desirable to provide an injector to entrain cabin air for demist purposes which did not create negative pressure downstream of the CBW filter and the possibility of inward chemical agent leakage.

SUMMARY AND OBJECTS OF THE INVENTION

According to the invention, an injector mechanism utilizes LOX, GOX, or OBOGS gas to supply the primary energy to entrain aircraft cabin air and pass it through a CBW filter prior to delivery of the gas to a CBW hood and visor. The injector reduces breathing gas consumption for the demist function typically by 75 percent or more and eliminates the need for a separate filter-blower during flight. The present invention locates the filter downstream of the injector to ensure that a positive pressure always exists between the filter and the pilot to preclude any inward leakage which would jeopardize the systems's chemical protection effectiveness. Any leakage downstream of the proposed injector will be outward from the life support system as a result of the constant positive pressure.

The demist injector may be equipped with a manually adjustable valve which limits the flow of the breathing gas through the injector and results in regulation of the entrained cabin air and the total gas flow to the CBW hood and visor. The injector may also be equipped with an evacuated bellows (aneroid) which senses the aircraft cabin ambient pressure and controls the supply pressure to the manually adjustable valve. This limits the oxygen flow through the injector as a function of aircraft cabin pressure to provide a relatively constant volumetric flow rate at all altitudes and eliminates the need to manually adjust the flow rate as the aircraft altitude changes.

The demist injector may be integrated into a typical man-mounted oxygen breathing regulator to minimize size and weight. Integration with the breathing regulator allows both components to share a common breathing gas source of supply and eliminates the need for a separate gas supply line for the injector mechanism.

Alternatively, the demist injector may be attached to a man-mounted oxygen breathing regulator as an external module to reduce the nonrecurring cost of implementing a CBW compatible life supply system. The combination with the man-mounted breathing regulator as an external module allows both components to share a common breathing gas source of supply and eliminates the need for a separate gas supply line for the injector mechanism.

It is, accordingly, an object of the invention to provide a demist injector to entrain cabin air for delivery to a CBW filter and the hood and visor of an aircrew CBW suit.

It is another object of the invention to provide a demist injector using oxygen supply gas to supply the primary energy to entrain cabin air upstream of a CBW filter for use in demisting a CBW hood and visor.

It is another object of the invention to provide an injector system to entrain cabin air upstream of a CBW filter to prevent negative pressure downstream of the CBW filter and eliminate drawing unfiltered air into the demist gas stream.

These and other objects of the invention will be apparent from the following detailed description in which reference numerals used throughout the description correspond to numerals found on the drawing figures.

BRIEF DESCRIPTION OF THE DRAWINGS

FIG. 1 is a schematic illustration of a CBW breathing system using the injector of the invention.

FIG. 2 shows the injector of the invention.

DESCRIPTION OF THE PREFERRED EMBODIMENT

Referring now to the drawing figures, FIG. 1 is a schematic illustration 10 of a breathing gas supply using a CBW filter injector mechanism according to the invention. A breathing gas supply 12 may comprise LOX, GOX, or OBOGS as desired. The breathing gas from the supply 12 is coupled to the inlet 13 of an injector 14 and to a pilot's regulator 16. The output of the regulator 16 is coupled to a breathing mask 19 under the hood 20 of an aircrew flight suit. The injector 14 includes an ambient air inlet 17 and an outlet 21 which is coupled by a conduit 23 to a CBW filter 24, the outlet 25 of which is connected to the hood and visor demist coupling 26 on the hood 20. The injector 14 and the regulator 16 are schematically shown as joined together although the two devices may be physically separated without departing from the spirit of the invention.

Referring now to FIG. 2, the injector 14 comprises a body 28 having an inlet 13 which leads to the inlet passage 29 of a pressure reducer 30. The pressure reducer 30 develops a regulated pressure in the control chamber 31 formed on one side of a piston 32. A push rod 33 rests against the top of the piston 32 and is driven by the expansion or contraction of an aneroid 34. The aneroid is mounted in a separate chamber 35 which is coupled to ambient by a vent passage 36. The piston 32 is biased by a control spring 37, and the underside of the piston 32 is vented to ambient by means of a vent port 38. The control chamber 31 is coupled by a passageway 39 to a needle valve 40 comprising a movable needle 41 and an orifice 42. The needle 41 comprises a threaded shaft 43 and a tapered end 44 which moves relative to the orifice 42. The outlet of the needle valve is coupled to an injector chamber 46 which leads to an injector nozzle 50. The injector nozzle 50 is positioned at one end of a mixing chamber 51 which receives ambient air from the ambient air inlet 17. The mixing chamber 51 is coupled to the injector outlet 21, and the conduit 23 couples the injector outlet 21 to the CBW filter 24. The outlet 25 of the CBW filter 24 is coupled to the hood and visor demist coupling 26 as shown in FIG. 1.

METHOD OF OPERATION OF THE PREFERRED EMBODIMENT

The breathing gas supply 12 supplies breathing gas to the injector inlet 13 and through the inlet passage 29 to the control chamber 31 of the pressure reducer 30. Air from the control chamber 31 flows through the passageway 39 and the needle valve 40 to the injector chamber 46. The flow of air from the chamber 46 through the injector nozzle 50 creates a low pressure region in the mixing chamber 51 which draws ambient air through the ambient air inlet 17. The resulting mixture of injector gas and ambient air in the chamber 51 passes through the injector outlet 21, through the conduit 23, and to the CBW filter 24. The gas mixture is scrubbed and purified by the CBW filter 24 and flows to the filter outlet 25 and to the hood and visor demist inlet 26 on the aircraft crew hood 20.

The operation of the pressure reducer 30 is altitude compensated by the aneroid 34 acting through the pushrod 33. An aneroid 34 comprises an evacuated bellows which is mounted in the body of the injector and exposed to ambient pressure by means of the vent passage 36. Motion of the aneroid 34 in response to ambient pressure changes is coupled to the piston 32 by the pushrod 33. The demist flow rate through the system may be varied by adjustment of the position of the taper 44 of the needle valve 40 in the orifice 42. Once this adjustment has been made, the aneroid 24 controls the absolute pressure delivered to the needle valve 40, thereby automatically controlling the volumetric flow rate through the injector 14 as the altitude changes.

Through the use of the invention, the volume of breathing gas which is required to demist and defog the visor of a CBW helmet is reduced by 75 percent, without the necessity of an auxiliary blower. Additionally, any contamination which enters the air stream at the low pressure mixing chamber 51 is removed by the downstream CBW filter 24. The system maintains positive pressure between the CBW filter 24 and the aircrew hood 20 ensuring that any leakage path results in outward flow to ambient rather than inward flow into the hood air supply.

Having thus described the invention, various alterations and modifications will be apparent to those skilled in the art, which modifications and alterations are intended to be within the scope of the invention as defined by the appended claims.

What is claimed is:

1. An injector for providing a gas stream to demist and defog a hood visor assembly of an aircrew chemical and biological warfare ("CBW") suit, the injector comprising:
- an inlet for supply gas under pressure and a pressure reducer having a control chamber located at said inlet;
- means for altitude compensating the pressure reducer;
- a passageway coupling the control chamber to an injector cavity;
- a flow controller in the passageway, said flow controller comprising a needle value;
- a manual adjustment means for the needle valve;
- an injector nozzle coupled to the injector cavity, said injector nozzle injecting gas from the injector cavity into a mixing chamber and causing low pressure in the mixing chamber;
- an ambient air inlet coupled to the mixing chamber, the low pressure caused in the mixing chamber by the injector nozzle drawing ambient air into the mixing chamber;
- an injector outlet coupled to the mixing chamber;
- a CBW filter coupled to and downstream of the injector outlet and downstream of the low pressure caused by the injector nozzle; and
- means coupling the outlet of the CBW filter to said hood and visor assembly, the gas mixture delivered to the CBW filter comprising a major portion of ambient air and a minor portion of supply gas.

2. An injector for providing a gas stream to demist and defog a hood and visor assembly of an aircrew chemical and biological warfare ("CBW") suit, the injector comprising:
- an inlet for supply gas under pressure and a pressure reducer having a control chamber located at said inlet;
- aneroid means for altitude compensation of the pressure reducer;
- a movable piston in the pressure reducer;
- a cavity vented to ambient and an injector mounted in the cavity;
- a pushrod between the aneroid means and the movable piston said pushrod coupling expansion or contraction of the aneroid means to the movable piston;
- a passageway coupling the control chamber to an injector cavity;
- a flow controller in the passageway, said flow controller comprising a needle valve;
- an injector nozzle coupled to the injector cavity, said injector nozzle injecting gas from the injector cavity into a mixing chamber and causing low pressure in the mixing chamber;

an ambient air inlet coupled to the mixing chamber, the low pressure caused in the mixing chamber by the injector nozzle drawing ambient air into the mixing chamber;

an injector outlet coupled to the mixing chamber;

a CBW filter coupled to and downstream of the injector outlet and downstream of the low pressure caused by the injector nozzle; and means coupling the coupling the outlet of the CBW filter to said hood and visor assembly, the gas mixture delivered to the CBW filter comprising a major portion of ambient air and a minor portion of supply gas.

* * * * *